US00PP20511P3

(12) United States Plant Patent
Southwick et al.

(10) Patent No.: US PP20,511 P3
(45) Date of Patent: Dec. 1, 2009

(54) APRICOT TREE NAMED 'SC2'

(50) Latin Name: *Prunus armeniaca*
Varietal Denomination: SC2

(75) Inventors: Stephen M. Southwick, Lodi, CA (US); David Decalo, Boulder, CO (US)

(73) Assignee: SDR Fruit, LLC, Boulder, CO (US)

( * ) Notice: Subject to any disclaimer, the term of this patent is extended or adjusted under 35 U.S.C. 154(b) by 97 days.

(21) Appl. No.: 12/002,418

(22) Filed: Dec. 17, 2007

(65) Prior Publication Data

US 2009/0158477 P1 Jun. 18, 2009

(51) Int. Cl.
*A01H 5/00* (2006.01)

(52) U.S. Cl. ..... Plt./186

(58) Field of Classification Search ..... Plt./186
See application file for complete search history.

*Primary Examiner*—Susan B McCormick Ewoldt
(74) *Attorney, Agent, or Firm*—Wells St. John PS

(57) ABSTRACT

A new and distinct variety of apricot tree, denominated varietally as 'SC2' is disclosed and which is mature for harvesting and shipment under the ecological conditions prevailing in the San Joaquin Valley of California about May 3$^{rd}$ to May 10$^{th}$.

3 Drawing Sheets

Botanical classification: *Prunus armeniaca.*

BACKGROUND OF THE NEW VARIETY

The present invention relates to a new and distinct variety of apricot tree, '*Prunus armeniaca* L' and which has been denominated varietally as 'SC2', hereinafter, and more specifically to an apricot tree variety which is characterized as to novelty by bearing medium to large fruit which ripen early in the season, and develop under low chilling hour conditions, and which further has a smooth skin, and a bright red blush, and wherein the present variety is ripe for harvesting and shipment approximately May 3–May 10 under the ecological conditions prevailing in the San Joaquin Valley of California.

ORIGIN AND ASEXUAL REPRODUCTION

The present variety of apricot was originated by the inventors from a chance open pollinated apricot cultivar named 'OrangeRed' (unpatented) and which is sometimes referred to as 'Bhart' in Europe, and which was found in a cultivated area in Vina, Calif. in 1993. Open pollinated seed derived from the newly discovered chance open pollinated cultivar 'OrangeRed' was germinated, and planted in 1994, by the inventors at an orchard which is located in Vina, Calif., in the northern portion of the San Joaquin Valley. The resulting tree grown from the open pollinated seed derived from the earlier mentioned chance open pollinated cultivar of 'OrangeRed' (unpatented) showed promising characteristics and was thereafter selected for propagation. The inventors first observed fruit produced from the new variety of apricot tree during the 1996 and 1997 growing seasons. The new variety of apricot tree was first asexually reproduced by budding in 1998. In this regard, bud wood from the new variety was first budded onto 'Lovell' peach rootstock (unpatented). These second generation trees were planted on a ranch which is located near Bakersfield, Calif. in the southern portion of the San Joaquin Valley. These asexually reproduced trees have been continually observed and compared and contrasted with the original chance, open pollinated seedling and it has been subsequently determined that the characteristics of the original chance open pollinated seedling have been transmitted to the subsequent asexually reproduced trees.

SUMMARY OF THE VARIETY

The new variety of apricot tree 'SC2' is characterized as to novelty, and is otherwise deemed noteworthy, by producing fruit which are ripe for commercial harvesting and shipment approximately May 3–May 10 under the ecological conditions prevailing in the San Joaquin Valley of California. As compared to the fruit harvested from the 'OrangeRed' and 'Castlebrite' apricot trees (both unpatented) growing in the same geographical region, the present variety is harvested about 10 days earlier than the apricot variety 'Castlebrite', and 5–7 days earlier than the 'OrangeRed' apricot trees growing at the same geographical location. Further, the new variety produces larger fruit in relative comparison to the 'OrangeRed' apricot trees growing in the same geographical location. Moreover, the tree of the present variety thrives under high summer temperatures, which sometimes exceed 45 degrees C., and additionally is a consistent producer of high quality fruit under the low chilling hours environmental conditions prevailing in such locations as Bakersfield, Calif.

BRIEF DESCRIPTION OF THE DRAWINGS

The accompanying drawings are color photographs of various aspects of the present plant. The colors are as nearly true as reasonably possible in color representations of this type. Due to chemical development, processing and printing, the leaves and fruit of the present tree may or may not be accurate when compared to the actual specimen. For this reason, future color references should be made to the color plates as provided by The Royal Horticultural Society Colour chart and other general color descriptions as provided for hereinafter.

DETAILED DESCRIPTION

Figure 1:
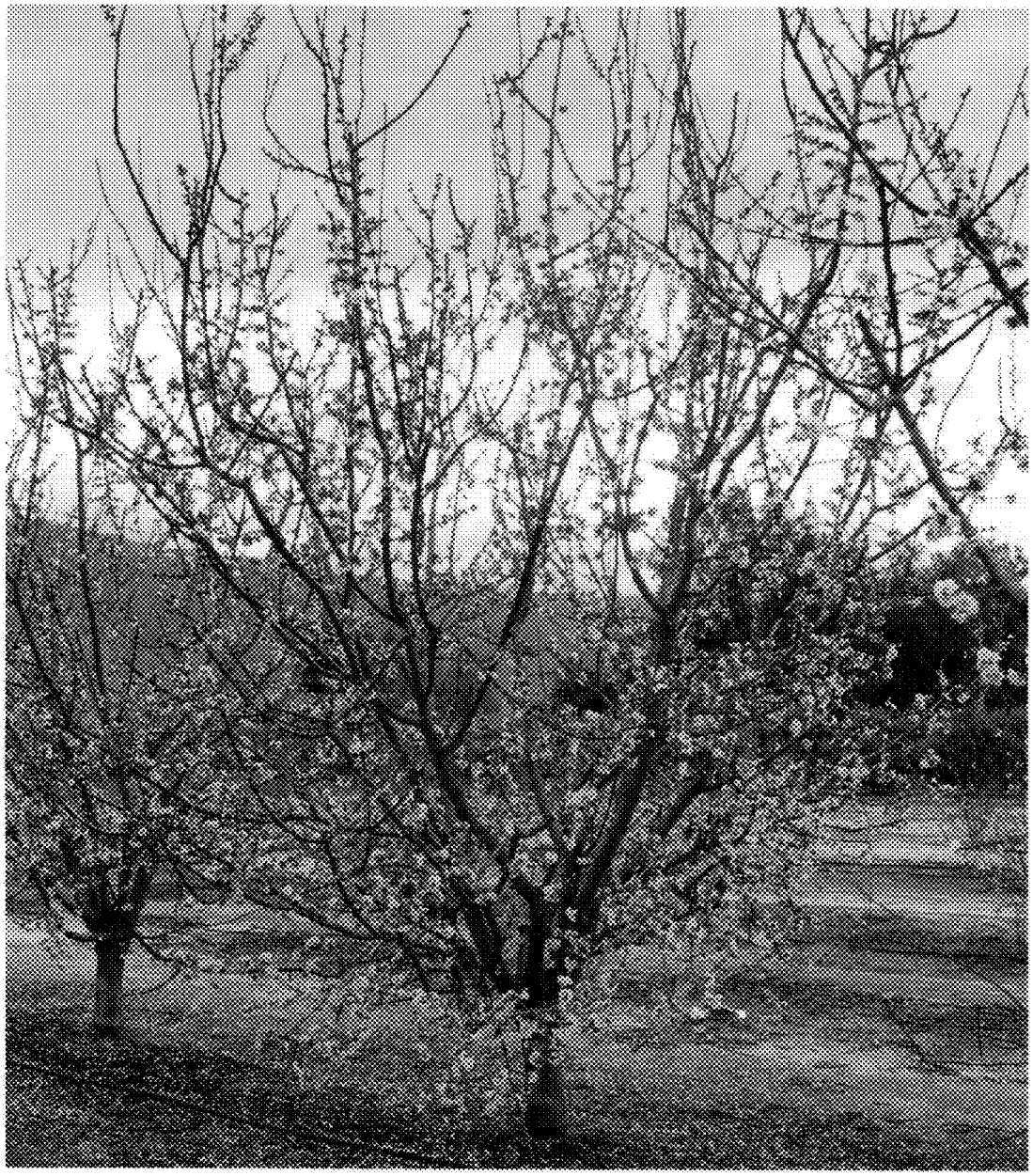
FIG. 1 illustrates the growing habit of a nine year old, second generation tree of the new variety of apricot tree as presently growing during the 2007 growing season near Bakersfield, Calif.
Figure 2:
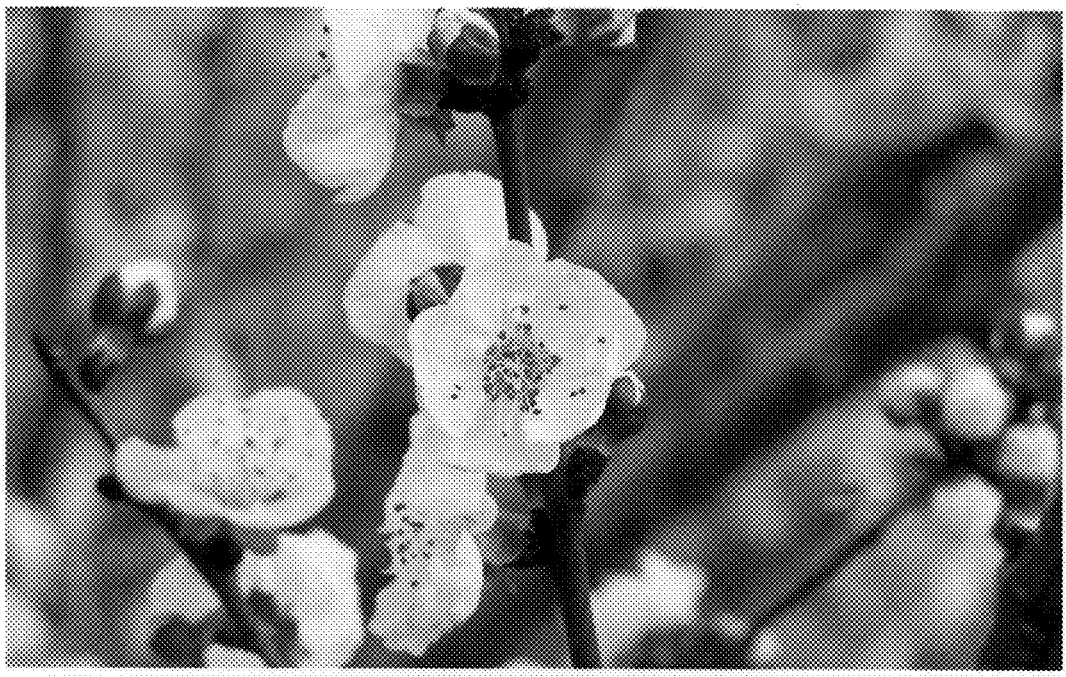
FIG. 2 shows the bloom characteristics of the 'SC2' apricot tree during the 2007 growing season.
Figure 3:
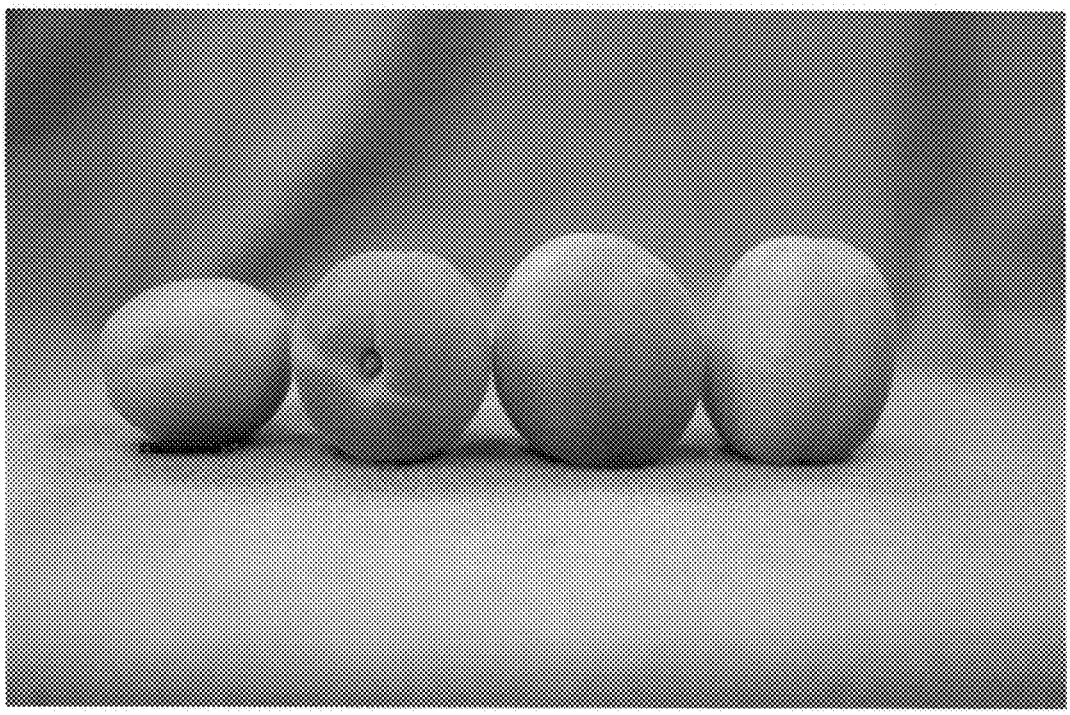
FIG. 3 shows several fruit of the present variety in different orientations.
Figure 4:
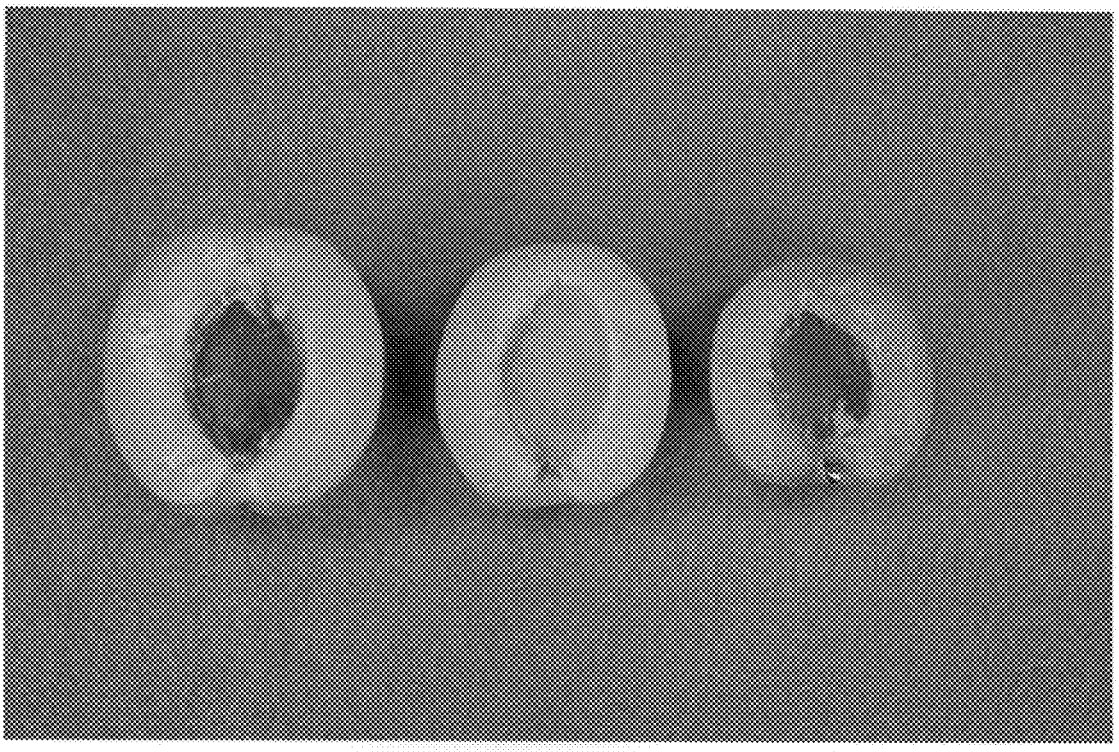
FIG. 4 shows several mature fruit of the subject variety which have been dissected in the axial plane to show the flesh and stone characteristics thereof.

Referring more specifically to the pomological details of this new and distinct variety of apricot tree, the following has been observed on a nine year old, second generation tree, under the ecological conditions prevailing at an orchard which is located near Bakersfield, Calif. All major color codes are by reference to the R.H.S. Colour Chart ($4^{th}$ Edition) provided by The Royal Horticultural Society of Great Britain. Common color names are also occasionally used.

NOT A COMMERCIAL WARRANTY

The following detailed description has been prepared to solely comply with the provisions of 35 U.S.C. §112, and does not constitute a commercial warranty, (either expressed or implied) that the present variety will in the future display the botanical, pomological or other characteristics as set forth hereinafter. Therefore, this disclosure may not be relied upon to support any future legal claims including, but not limited to, breach of warranty for merchantability, or fitness for any particular purpose which is directed, in whole or in part, to the present variety.

TREE

*Size.*—Considered average for the variety. The tree which was inspected was a nine year old second generation tree growing on 'Lovell' (unpatented) peach seedling rootstock, and which had attained a height of about 5.5 meters; and a width dimension of approximately 3.5 meters.

*Vigor.*—Considered moderately high with an annual growth of about 0.25 meters to about 1.25 meters.

*Growth habit.*—Considered more upright than upright-spreading. The variety has a regular branching pattern.

*Form.*—Upright and pruned into a vase shape.

*Productivity.*—Considered highly productive. Depending upon the fruit set of the tree, thinning will typically be annually required for fruit of the new tree to reach full commercial size.

*Regularity of bearing.*—Regular. This occurs even in seasons which have low chilling conditions. The tree is considered precocious in its fruit production.

*Fertility.*—The variety is not self-fertile, but requires cross-pollination from a compatible cultivar having approximately the same bloom time.

*Canopy density.*—Considered dense. The present variety requires seasonal pruning to maintain the vase shape, and keep the tree open for light penetration to maintain spur development and proper development of fruit to an appropriate commercial size.

*Hardiness.*—Considered hardy when grown under the ecological conditions prevailing in the San Joaquin Valley of California. The present tree thrives under high (exceeding 45 degrees C.) summer temperatures.

*Chilling requirements.*—This variety requires about 525 to about 575 hours at a temperature below 7.2° C. to permit the variety to flower in a normal fashion.

TRUNK

*Diameter.*—About 33 cm. when measured about 30 cm. above the surface of the earth.

*Bark texture.*—Rough.

*Trunk bark color.*—The outer ridges of the bark color is grey (Group N200); valleys in the bark are considered brown (Group N200B).

BRANCHES

*Scaffold branches.*—Generally — When measured at a distance of about 90 cm. above the soil line, the scaffold braches have a bark texture which is considered mostly smooth.

*Scaffold branch bark color.*—Grey (Group 201A).

*Lenticels.*—Size — About 1–1.5 mm. in width, and about 3.75–6.9 mm. in length.

*Lenticels.*—Color — Considered grey-white (Group 156D).

*Flowering branches.*—Diameter — About 4.5 mm.

*Flowering branches.*—Texture — Glabrous.

*Flowering branches.*—Color — Grey-orange (Group 173A).

*Flowering branches.*—Lenticels — Present and considered moderate in number, and ranging in count from about 10–15 lenticels per linear cm. as measured at approximately the mid-point of a flowering branch.

*Lenticel color.*—White (Group 155C).

*Internodes.*—Length — Approximately 1.35 cm. to about 2.1 cm.

LEAVES

*Leaf form.*—Generally — Flat and broadly oval.

*Marginal form.*—Finely crenate and approaching crenulate.

*Tip.*—Shape — Mucuronate.

*Base.*—Shape — Rounded.

*Leaf size.*—Average length — About 89.5 mm.

*Leaf size.*—Width — About 80.1 mm.

*Leaf thickness.*—Average for the species.

*Leaf color.*—Upper surface — Yellow-green (Group 147A).

*Leaf color.*—Lower surface — Yellow-green (Group 148A).

*Petiole.*—Size — The average length, is about 40.6 mm.

*Petiole.*—Diameter — About 1.56 mm.

*Petiole.*—Color — Yellow-green (Group 145D). The upper surface near the abscission end exhibits a reddish blush (Group 183B).

*Leaf glands.*—Petiole — 1–3 leaf glands are normally found.

*Leaf glands.*—Shape — Globose in form, and having an average width of about 0.2 mm. and an average length of about 1.5 mm.

*Leaf glands.*—Position — Alternate, and seen on the dorsal surface of the petiole, close to the blade.

*Leaf glands.*—Color — Black (Group 202A).

*Leaf stipules.*—Absent.

*Leaf venation.*—Pinnately net veined.

*Leaf buds.*—Shape — Ovoid.

*Leaf buds.*—Size — About 2.5 mm. wide, and about 3.2 mm. long.

*Leaf bud color.*—Considered Gray-purple (Group N186A).

FLOWERS

*Date of first bloom.*—On or about Feb. 23, 2007 under the ecological conditions prevailing near Bakersfield, Calif.

*Date of full bloom.*—Feb. 27, 2007 under the ecological conditions prevailing near Bakersfield, Calif.

*Flower buds.*—Shape — Ovoid.

*Flower buds.*—Size — About 2.9 mm. wide; and about 4.5 mm. long.

*Flower buds.*—Color — Gray-purple (Group N186A).

*Flower size.*—At full expansion, the average diameter is about 2.37 cm.

*Flower aroma.*—Generally speaking, while an aroma is present, it is very slight or considered mild, and typical of apricot trees, in general.

*Flower petals.*—Numbers — 5.

*Flower petals.*—Arrangement — Considered overlapping.

*Flower petals.*—Shape — Flat-round.

*Flower petals.*—Length — About 10 mm. to about 14.1 mm.

*Flower petals.*—Width — About 13.2 mm. to about 17.4 mm.

*Flower petals.*—Apex — The apex is rounded.

*Flower petals.*—Base — The shape of the base is round but narrows at the attachment point.

*Receptacle.*—Peduncle — About 1.4 mm. in length; about 1.8 mm. in diameter; and having a green color (Group 139D).

*Flower petals.*—Surface Texture — Glabrous.

*Flower petals.*—Margins — Considered smooth.

*Flower petals.*—Color — White with a faint red-purple color around the margins (Group 69A).

*Sepals.*—Numbers — 5.

*Sepals.*—Shape — Oval with a cuspidate apex. The outer margins cup inwardly.

*Sepals.*—Length — About 5.5 mm. to about 6.6 mm.

*Sepals.*—Width — About 4.5 mm. to about 5.7 mm.

*Sepals.*—Surface texture — Considered glabrous.

*Sepals.*—Color — Red-purple (Group 60A).

*Stamens.*—Numbers — Variable from about 30 to 33.

*Stamens.*—Average length — About 10 mm.

*Stamens.*—Filament length — About 9 mm.

*Filament color.*—White (Group 155C).

*Anther length.*—About 1 mm.

*Anther color.*—Yellow (Group 12B).

*Mature pollen color.*—Yellow (Group 12B).

*Pistil.*—Numbers — 1.

*Pistil.*—Length — About 12.5 mm.

*Ovary.*—Size — About 2.7 mm. in diameter.

*Ovary color.*—Green (Group 139D).

*Ovary pubescence.*—Present.

*Stigma.*—Length — About 10.1 mm.

*Stigma.*—Color — Yellow (Group 3B).

*Thalamus.*—Size — About 5.3 mm. in length; and about 4.6 mm. in width.

*Thalamus.*—Color — Yellow-green (Group 150C). Further, the base is highlighted with a red-purple color (Group 60A) at the sepal attachment.

FRUIT

*Maturity.*—When described, firm, ripe condition, that is (shipping ripe). Date of first picking May 3, 2007.

*Date of last pick.*—May 10, 2007. The aforementioned harvesting dates are under the ecological conditions prevailing near Bakersfield, Calif.

*Fruit size.*—Considered average for the species.

*Average length.*—About 53 mm.

*Average diameter.*—About 48.4 mm. when measured at the suture.

*Average diameter perpendicular to the fruit suture.*—About 44.5 mm.

*Fruit weight.*—The average fruit weight of the new variety is approximately 63.2 grams.

*Fruit shape.*—Generally speaking it is considered round, and oblong.

*Stem cavity.*—Size — About 13.4 mm. wide; and about 9.2 mm. in depth. Only very light tearing is occasionally detected.

*Stem retention.*—Approximately 25% of the stem is retained.

*Fruit suture.*—Generally — Present, and shallow with a depth of less than about 0.75 mm.

*Fruit skin.*—Texture — Considered smooth and is resistant to cracking caused by rain.

*Fruit skin.*—Thickness — Considered thin, tender and melting.

*Fruit skin.*—Pubescence — Present and very fine.

*Fruit skin.*—Color — The background color is orange (Group 26A). Additionally, a blush color develops and covers about 65%–75% of the skin area. This blush is red (Group 46A).

*Tendency to crack.*—Not observed.

*Flesh texture.*—Considered firm and moderately crisp.

*Flesh.*—Color — Orange (Group 26A).

*Flesh.*—Sugar Content — On average, about 13.8 degrees brix.

*Flesh.*—Aroma — Considered typical of apricots.

*Flavor.*—Mild, sweet and having a sub-acid character.

*Flesh fibers.*—Generally — Present, but sparse. The fibers are considered short and non-obtrusive.

*Eating quality.*—Considered excellent for both local and long distance commercial fresh markets.

STONE

*Generally.*—Considered to be a semi-clingstone.

*Stone length.*—About 30.7 mm.

*Stone diameter.*—When taken in the line of the suture, it is about 20.7 mm.

*Stone diameter.*—When taken at a position perpendicular to the suture, it is about 11 mm.

*Stone color.*—Fully dried — Grey-orange (Group 165B).

*Stone cavity.*—Length — About 32.9 mm.

*Stone cavity.*—Width — As measured at the suture, about 23.4 mm.

*Stone form.*—Generally — Considered ovate, and having equal halves when considered along the suture plane.

*Stone base.*—Shape — Rounded.

*Stone apex.*—Considered more conic than round.

*Stone ridges.*—Generally — Three distinct and sharp ridges extend from the apex to the base. The distance between the outside ridges at their widest point is, on average, about 9.7 mm.

*Stone surface.*—Textured.

*Tendency to split.*—The fruit which were inspected showed that about 35% of the stones had split at full commercial maturity.

*Resistance to insects and diseases.*—No particular susceptibilities were noted. The present variety has not been tested to expose or detect any susceptibilities or resistance of any known plant and/or fruit diseases.

Although the new variety of apricot possesses the described characteristics when grown under the ecological conditions prevailing in the San Joaquin Valley of California, it should be understood that variations of the usual magnitude and characteristics incident to changes in growing conditions, fertilization, pruning, pest control, and horticultural management are to be expected.

Having thus described and illustrated our new variety of apricot tree, what we claim is new, and desire to secure by Plant Letters Patent is:

1. A new and distinct variety of apricot tree substantially as shown and described and which is characterized principally as to novelty by having a date of harvesting which is about May $3^{rd}$ to May $10^{th}$ under the ecological conditions prevailing in the San Joaquin Valley of California.

* * * * *